United States Patent
Ienaga

(10) Patent No.: US 9,801,858 B2
(45) Date of Patent: Oct. 31, 2017

(54) PROGRESS-SUPRESSING OR IMPROVING AGENT FOR CHRONIC KIDNEY DISEASE

(71) Applicant: NIPPON ZOKI PHARMACEUTICAL CO., LTD., Osaka-shi, Osaka (JP)

(72) Inventor: Kazuharu Ienaga, Osaka (JP)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/122,082

(22) PCT Filed: Feb. 25, 2015

(86) PCT No.: PCT/JP2015/055397
§ 371 (c)(1),
(2) Date: Aug. 26, 2016

(87) PCT Pub. No.: WO2015/129750
PCT Pub. Date: Sep. 3, 2015

(65) Prior Publication Data
US 2017/0065563 A1 Mar. 9, 2017

(30) Foreign Application Priority Data
Feb. 26, 2014 (JP) ................. 2014-034792

(51) Int. Cl.
| A61K 31/4166 | (2006.01) |
| A61K 9/20 | (2006.01) |
| A61K 9/28 | (2006.01) |
| A61K 9/00 | (2006.01) |

(52) U.S. Cl.
CPC ........ *A61K 31/4166* (2013.01); *A61K 9/0053* (2013.01); *A61K 9/2009* (2013.01); *A61K 9/2013* (2013.01); *A61K 9/2054* (2013.01); *A61K 9/2813* (2013.01); *A61K 9/2853* (2013.01); *A61K 9/2866* (2013.01)

(58) Field of Classification Search
CPC .............. A61K 31/4166; A61K 9/0053; A61K 9/2009; A61K 9/2013; A61K 9/2054; A61K 9/2813; A61K 9/2853; A61K 9/2866

USPC ...................................................... 548/300.1
See application file for complete search history.

(56) References Cited

U.S. PATENT DOCUMENTS

| 5,084,473 A | 1/1992 | Mikami et al. |
| 7,569,701 B2 | 8/2009 | Okamoto et al. |
| 7,858,806 B2 | 12/2010 | Okamoto et al. |
| 2005/0143437 A1 | 6/2005 | Okamoto et al. |
| 2009/0270634 A1 | 10/2009 | Okamoto et al. |

FOREIGN PATENT DOCUMENTS

| JP | S57-114578 A | 7/1982 |
| JP | H03-72463 A | 3/1991 |
| WO | 03/084934 A1 | 10/2003 |

OTHER PUBLICATIONS

Nakano et al.; "Effect of NZ-419 on Diabetic Chronic Renal Failure;" J Am Soc Nephrol; 1999; pp. 131A, A0675; vol. 10.
Nakano et al.; "Effect of NZ-419 on Diabetic Chronic Renal Failure;" XV International Congress of Nephrology, Buenos Aires; 1997; pp. 385.
Ienaga et al.; "Treatment with NZ-419 (5-Hydroxy-1-methylimidazoline-2,4-dione), a Novel Instrinsic Antioxidant, against the Progression of Chronic Kidney Disease at Stages 3 and 4 in Rats;" Biol. Pharm. Bull.; 2010; pp. 809-815; vol. 33, No. 5.
May 19, 2015 Search Report issued in International Application No. PCT/JP2015/055397.

*Primary Examiner* — Kristin Vajda
(74) *Attorney, Agent, or Firm* — Oliff PLC

(57) ABSTRACT

An object of the present invention is to provide a pharmaceutical agent which is administered to a patient with chronic kidney disease in which the progress of worsening of renal function is rapid whereby the progress of the symptom is suppressed or improved.

The present invention relates to a progress-suppressing or improving agent for chronic kidney disease containing 5-hydroxy-1-methylhydantoin as an active ingredient. The pharmaceutical agent of the present invention showed a significant effect in a patient with chronic kidney disease where progress of the renal function decrease is rapid. The present pharmaceutical agent is very useful as a highly safe pharmaceutical agent which suppresses or improves the progress of worsening of the renal function of a patient with rapidly progressive chronic kidney disease for which there has been no effective therapeutic agent being simply and easily ingestible.

10 Claims, 2 Drawing Sheets

Figures
[Fig. 1]
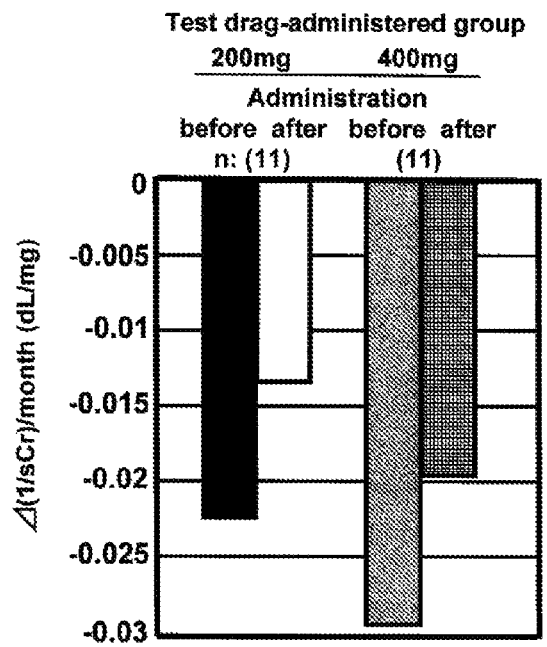
[Fig. 2]
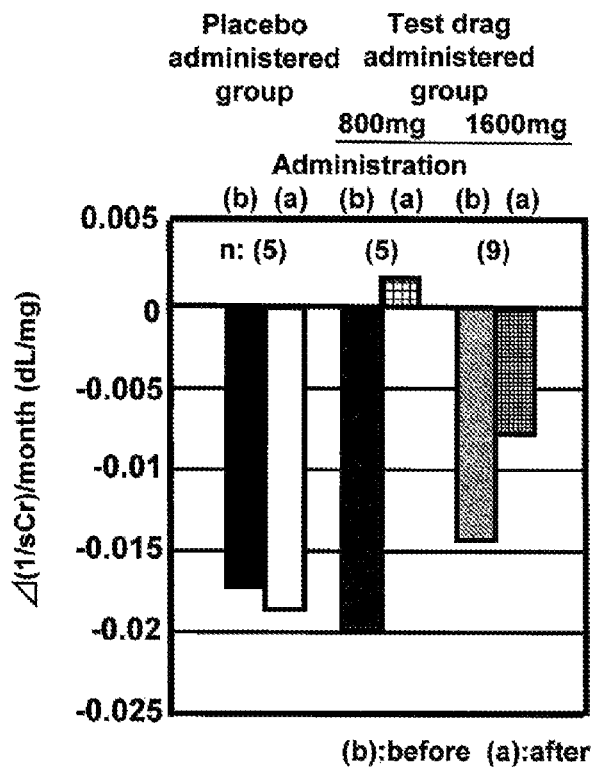

[Fig. 3]
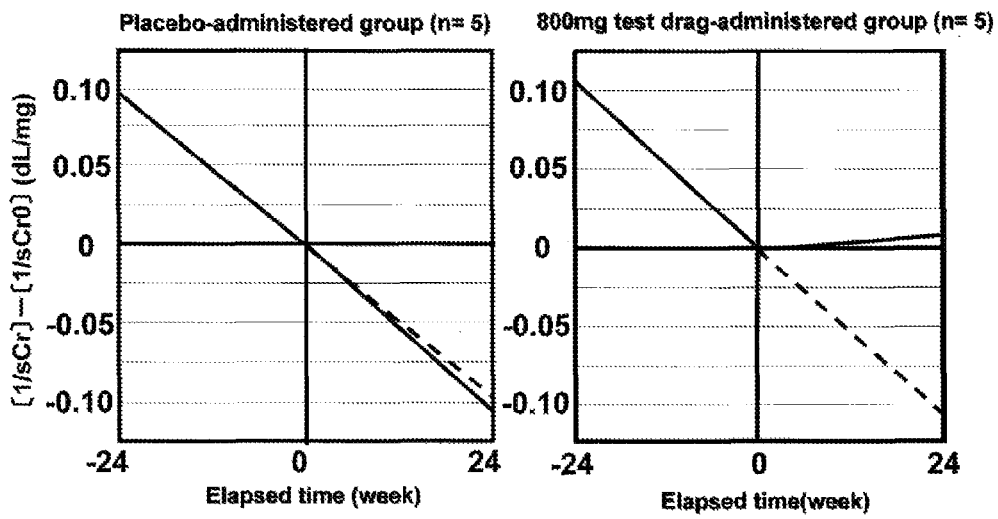
[Fig. 4]
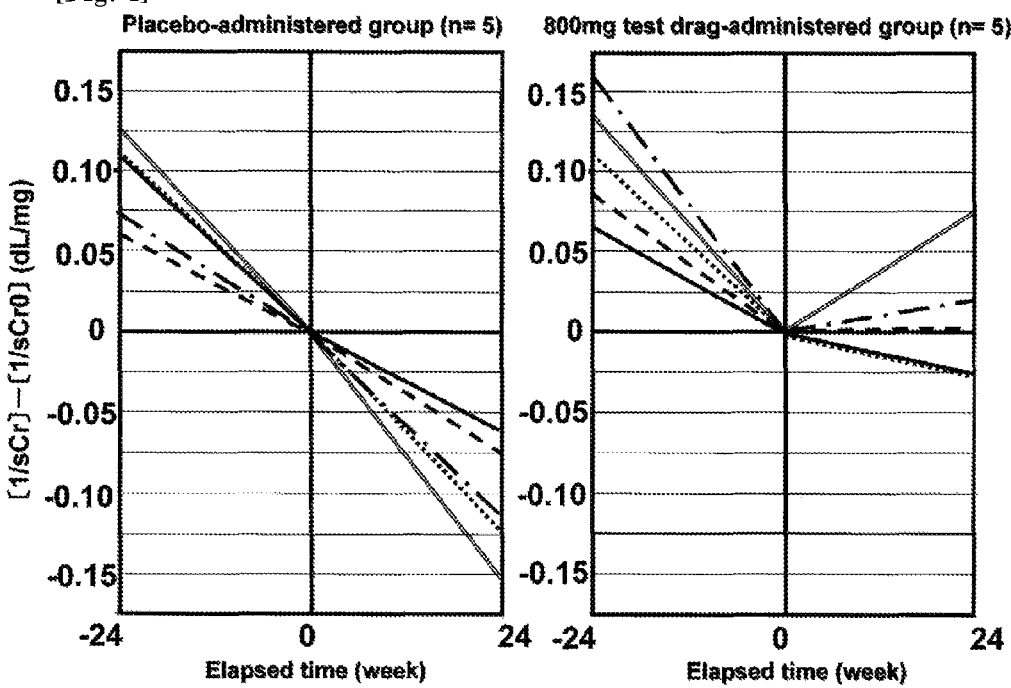

PROGRESS-SUPRESSING OR IMPROVING AGENT FOR CHRONIC KIDNEY DISEASE

TECHNICAL FIELD

The present invention relates to a progress-suppressing or improving agent for chronic kidney disease containing 5-hydroxy-1-methylhydantoin (IUPAC name: 5-hydroxy-1-methylimidazolidin-2,4-dione) (hereinafter, it will be referred to as "the present compound") as an active ingredient.

BACKGROUND ART

Chronic kidney disease (CKD) is a relatively new concept for a disease proposed by the National Kidney Foundation (NKF) of the United States in 2002. As to the cause therefor, there are various systemic diseases and renal diseases and typical ones are diabetes mellitus, hypertension, chronic nephritis, etc. CKD is defined as such ones where any of the following (1) and (2) or both continue(s) for three months or more. They are:

(1) The case where the existence of nephropathy is clear as a result of urine test, image and pathological diagnosis, blood test, etc. and particularly where not less than 0.15 g/gCr of proteinuria (not less than 30 g/gCr of albuminuria) is detected. (The unit "/gCr" means "per gram of creatinine".)

(2) The case where glomerular filtration rate (GFR) lowers to an extent of less than 60 mL/minute/1.73 $m^2$. (GFR will be mentioned later.)

As a result of an increase in the occurrence frequency of life style-related diseases such as diabetes mellitus and hypertension in recent years, CKD is also increasing steadily. For example, it has been mentioned that the numbers of patients with CKD in Japan are 13,300,000 and reaches about 13% (one patient in about eight persons) of the adult population ("Guide for Diagnosis of CKD—2012" edited by the Japanese Society of Nephrology).

The first problem when one suffers from CKD is that the renal function lowers whereby waste products and water are unable to be excreted. As a result, dropsy is generated or one feels languid. In addition, vomiting, headache and anorexia are resulted due to uremia. Further progress thereof induces complications such as cardiovascular diseases (CVD) such as myocardial infarction, cardiac failure and cerebral apoplexy and pulmonary edema whereby crisis of life becomes high.

When end-stage kidney disease (ESKD) is resulted as the progress of the CKD, dialysis and kidney transplantation are necessary. For example, in Japan, patients who need the dialysis are steadily increasing and, in 2011, they were more than 300,000. That is one of the causes of swelling the national medical expenses and is a big problem in view of medical economy as well. Moreover, because dialysis treatment is to be done usually three times a week and requires four to five hours for each dialysis, that is a big burden in the daily life of a patient and greatly deteriorates the QOL. Accordingly, it is important to try not to result in a state where the dialysis treatment is necessary due to the occurrence of ESKD and also to try to retard the stage of initiating the dialysis treatment as long as possible. (The CKD before the start of the dialysis treatment as such is called "CKD in a conservative stage".) In view of the above, there has been a brisk demand for pharmaceutical agents having a suppressive effect for the progress of CKD and exhibiting a high safety.

Human renal function is expressed by a glomerulus rate (CFR) which is the amount of plasma per unit time by all glomerular bodies in the kidney. A decrease in GFR means a decrease in the renal function. As a result thereof, metabolites in the body such as creatinine (Cr) and blood urea nitrogen (BUN) are unable to be excreted into urine but are accumulated in the body. As a reflection thereby, data of creatinine and BUN become high in the blood test. For precisely measuring the GFR, a troublesome test called inulin clearance or creatinine clearance is necessary. However, in the daily diagnosis where such a test is difficult, there has been used a simplified method in which serum creatine (sCr) value is measured by a blood test and, based on said value together with age and sex, an estimated glomerular filtration rate (eGFR) is calculated. For example, a calculation formula for eGFR suitable for the Japanese is proposed in "Evidence-based Practice Guidelines for the treatment of CKD—2013" edited by the Japanese Society of Nephrology), etc. In addition, the stage of CKD is roughly classified into five (the first stage to the fifth stage). Since the GFR value in the third stage (stage 3) or higher is less than 60 mL/minute/1.73 $m^2$ (as hereinafter, the unit for the GFR value will be omitted), that is the CKD (refer to the above definition for CKD in (2)). When the GFR is less than 15, that is the fifth stage (stage 5) and is ESKD.

The GFR value in a healthy person is 60 or more. In a patient with CKD of stage 3 and more where the GFR value is less than 60, metabolites such as creatinine begin to be accumulated in blood whereby serum creatinine value and blood urea nitrogen value begin to rise significantly. In a slowly progressive patient where the GFR value worsens to an extent of only less than 10 in one year, the time until becoming ESKD whereby dialysis is to be introduced is still left to some extent. In such a patient, there is conducted a measure where progress of the disease is made to retard by a therapy where blood pressure and blood sugar are normalized, a smoking cessation therapy and a diet therapy where ingestion of salt and protein is restricted so as to prevent to become ESKD (Therapies as such are called "conservative therapy" of CKD.). Since hypertension is the biggest risk factor for the occurrence and the progress of CKD and also for the occurrence of CVD, control of blood pressure is particularly important. As to an antihypertensive, angiotensin-converting enzyme (ACE) inhibitor and angiotensin II receptor blocker (ARB) have been mainly used in combination, depending upon a patient, with diuretic agent, calcium antagonist, etc.

The time-dependant changes of the renal function in CKD can be aware of by means of chronological plotting of the GFR values. Thus, when a graph is drawn where an ordinate is for the eGFR value while an abscissa is for the time (stage), a worsening speed of the renal function can be noted. It is general in CKD that the GFR value linearly lowers from upper left to lower right. When the slope of this line is made as small as possible by means of a diet therapy or a drug therapy, the stage where ESKD is resulted and a dialytic treatment is necessary can be retarded.

The time-dependant changes in the renal function in CKD is also able to be aware of by plotting the reciprocal serum creatine (sCr) values (1/sCr; hereinafter, it will be sometimes called "reciprocal sCr value"). That is because the reciprocal sCr value is proportional to the GFR value. When the renal function is evaluated by the sCr value, ranges of normal standard values are usually within a ranges of 0.5 to 1.1 mg/dL and 0.4 to 0.8 mg/dL (hereinafter, the unit will be omitted) for males and females, respectively. Since creatinine is produced in muscles, its amount is proportional to the muscle amount and, generally, that in males is higher than that in females to an extent of 10 to 20%. In addition, it rarely varies depending upon the age. In elderly persons, the renal glomerular filtration rate lowers with the age but, since the muscle amount also decreases therewith, the sCr value becomes nearly constant. In case the renal function is evaluated by means of the sCr value, a follow-up observation will be necessary in some cases when the values in male and female reach 1.2~1.3 and 0.9~1.0, respectively. Generally, in moderate CKD, the sCr value exceeds 1.5 and, in a critical condition, it is 2.4 or even more. When the sCr value exceeds 5, recovery is difficult and the stage where the sCr value is 10 is a yardstick for starting the dialysis. Generally, in the actual site of medical care, it is common that an appropriate treatment is investigated by observing the elapse of GFR values, reciprocal sCr values or sCr values for several months to know the worsening velocity of CKD of a patient.

In patients with CKD, there are those in such a type where slope of a straight line plotted by GFR values or that plotted by reciprocal sCr values (hereinafter, the latter will be called "slope of reciprocal sCr values") is relatively gentle and those in such a type where the slope is steep. For the former patients, it is possible to some extent to retard the progress to ESKD (to extend the period of CKD in a conservative stage) by a diet therapy or a drug therapy. However, for the patients where the GFR value or the reciprocal sCr value rapidly lowers and worsening of the symptom proceeds, there has been almost no therapeutic agent which effectively suppresses it. Once the patient reaches ESKD, dialysis is necessary in addition to a diet therapy and a drug therapy and QOL of the patient is very much deteriorated as mentioned already.

Under such circumstances, a spherical adsorptive carbon as a pharmaceutical agent has been approved in Japan where the indication is "improvement in uremic symptom in progressive chronic renal failure and retardation of introduction of dialysis". In short, this agent is activated carbon. When this agent is ingested (each 2 g, three times daily, 6 g in total), uremic toxin in a patient with CKD is adsorbed with an intestine and excreted together with feces whereby there is achieved an effect of improving the uremic symptom and of retarding the introduction of dialysis. For example, according to the package insert for "Kremezin (Registered Trade Mark)" which is the original spherical adsorptive carbon preparation in Japan, the slope of reciprocal sCr values was significantly improved to $-222\pm378\times10^{-5}$ dL/mg·week (hereinafter, the unit will be omitted) from $-329\pm245$ before the administration in a clinical test (double-blind test) where said preparation was administered in a daily dose of 6 g per day (three times 2 grams) for 24 weeks to "patients with progressive chronic renal failure". (In a placebo group, the data before and after the administration were $-293\pm184$ and $-274\pm279$, respectively.) In view of the above, there is no doubt that "Kremezin (Registered Trade Mark)" is an epoch-making drug which brought the big gospel to the patients with CKD. According to "Interview Form of Pharmaceutical Agent" for said agent, it has been sold in Asian countries such as Korea, Taiwan and the Philippines since its approval in Japan in 1991 although it has not been sold in Europe and America.

Incidentally, even a spherical adsorptive carbon preparation which is an epoch-making pharmaceutical agent, there are still some problems. Firstly, the spherical adsorptive carbon preparation has a problem that a dose of 6 g per day which is very high amount as a pharmaceutical agent should be ingested. Dosage forms of the spherical adsorptive carbon preparations sold in Japan are capsule and fine granules (powdered drug). With regard to the capsule, since one capsule contains 200 mg of the ingredient, one must ingest ten capsules at a time. Therefore, its daily dose is 30 capsules. Since that made the compliance of patients bad, another dosage form additionally approved in 2000 is fine granules (powdered drug). In the fine granules, since one pack contains 2 g, one pack at a time is ingested with water. When the fine granules are not well swallowed, the inner area of the mouth sometimes becomes entirely black. Therefore, it is recommended to swallow with some modifications such as to swallow after wrapping with a bag-shaped wafer (after dividing into several wafers if necessary) or to suck through a straw after being sunk in water in a cup. This should be conducted three times a day. In addition, it sometimes happens that, when the spherical adsorptive carbon preparation is ingested, the feces become black. In view of the above, there is a problem that the compliance upon ingestion of the spherical adsorptive carbon preparation is still bad. Moreover, the spherical adsorptive carbon preparation sometimes causes a side effect such as constipation or anorexia. When constipation happens, the effect of this drug decreases as well. In addition, since the spherical adsorptive carbon preparation adsorbs a chemical substance, when, for example, another pharmaceutical agent for hypertension or diabetes mellitus is administered together, there is a big problem that the active ingredient of the pharmaceutical agent is also adsorbed resulting in a decrease in the effect. Therefore, in a package insert for the spherical adsorptive carbon preparation, there is a description reading "When another agent is used together, it is to be taken into consideration that this agent is an adsorbent and the ingestion of another agent together with this agent should be avoided" as the "important fundamental notice" whereby ingestion together with another agent at the same time is prohibited. Under the current circumstances as such, there has been a brisk demand for the development of pharmaceutical agents for a patient with CKD where the effect is excellent, the side effect is little, the ingestion is easy and the simultaneous ingestion with another agent is possible.

The present compound (5-Hydroxy-1-methylhydantoin) was created by Nippon Zoki Pharmaceutical Co., Ltd. who is the applicant for the present application (Japan Patent Laid-Open No. sho-57-114578 and Japanese Patent No. 1,616,338). After that, the present compound was found to be effective for renal failure due to the suppression of production of uremic toxin (Patent Document 1). In Patent Document 1, there is described that the present compound has an action of lowering the uremic toxin such as urea nitrogen and creatinine in animal experiments using the rats with chronic renal failure induced by oral administration of adenine. However, there is no description therein at all for the optimum dose of the present compound to humans and also for the fact that, in case what type of a CKD-suffering patient is administered with the present compound, the effect for suppressing the progress of CKD can be significantly achieved.

In the meanwhile, the results of clinical tests of the present compound were presented at the meetings in 1997 and 1999 (Non-Patent Documents 1 and 2). In those documents, it is shown that the present compound suppresses the lowering of the reciprocal sCr value (1/sCr) of a patient with diabetic chronic renal failure (hereinafter, it will be referred to as "diabetic CRF"). However, pharmaceutical effects of the present compound are not compared after dividing the symptoms of patients into progressive and non-progressive ones. In addition, the effect of the present compound shown by those clinical test results cannot be said to be so significant and no development of the present compound has been conducted thereafter. Incidentally, the Non-Patent Documents 1 and 2 will be mentioned later in detail under the columns of Referential Example.

PRIOR ART DOCUMENTS

Patent Documents

Patent Document 1: Japanese Patent Laid-Open No. Hei-3-72463

Non-Patent Documents

Non-Patent Document 1: XVth International Congress of Nephrology, Buenos Aires, 385, 1997
Non-Patent Document 2: J. Am. Soc. Neph., 10, 131A, 1999

SUMMARY OF THE INVENTION

Problem to be Solved by the Invention

The problem of the present invention is to provide a very highly useful progress-suppressing or improving agent for CKD, where worsening of renal function of patients with rapidly progressive CKD for which no effective and easily ingestible therapeutic agent has been available up to now is able to be suppressed or improved.

Means for Solving the Problems

The present inventors have conducted the studies in more detail for the effect to CKD by means of clinical tests in CKD patients using a pharmaceutical agent containing the present compound as an active ingredient (hereinafter, the agent will be referred to as "the present agent"). As a result, it has been found that, when the present compound is ingested in a relatively high dose, a selective and significant effect is achieved for patients where lowering of renal function is rapidly progressing among the patients with CKD whereupon the present invention has been accomplished. In the present compound, toxicity is very low and almost no side effect is noted. Therefore, there was no problem in terms of safety for the patients with CKD to whom a relatively high dose was administered. In addition, the present agent can be administered orally and its simultaneous administration with another pharmaceutical agent is not denied as well. Therefore, the present agent is quite useful as a progress-suppressing and improving agent for CKD.

Advantages of the Invention

The present agent showed a significant effect in a selective manner to such a patient where lowering of renal function is rapidly progressing among the patients with CKD. Although dose of the present agent is relatively high, no side effect causing the inconvenience is found. Accordingly, the present agent is very highly useful as a pharmaceutical agent where worsening of renal function of patients with rapidly progressive CKD for whom no effective and easily ingestible therapeutic agent has been available can be suppressed or improved and, at the same time, safety is very high, ingestion is easy and simultaneous use with another pharmaceutical agent is not denied.

BRIEF DESCRIPTION OF DRAWINGS

FIG. 1 shows the result where the present compound was orally administered in a dose of 200 mg or 400 mg per day to patients with diabetic CRF and the changes in the renal function before and after the administration of the test drug were compared by means of inclination of regression lines to the reciprocal sCr values.

FIG. 2 shows the result where the placebo or the present compound was orally administered in a dose of 800 mg or 1600 mg per day to patients with CKD having different progressive property and the changes in the renal function before and after the administration were compared by means of inclination of regression lines to the reciprocal sCr values.

FIG. 3 is a graph showing the changes in the reciprocal inclination of sCr values when the placebo or the present compound was orally administered in a dose of 800 mg per day to patents with CKD where worsening of the renal function is rapidly progressing.

FIG. 4 is a graph showing the changes in the reciprocal inclinations of sCr values for all cases covering five test subjects of a placebo-administered group and five test subjects of a 800 mg/day of test drug-administered group.

MODE FOR CARRYING OUT THE INVENTION

The present invention relates to an agent for suppressing the progress of or for improving the chronic kidney disease (CKD) containing 5-hydroxy-1-methylhydantoin (the present compound) as an active ingredient With regard to 5-hydroxy-1-methylhydantoin (the present compound) which is an active ingredient in the present invention, there may be exemplified a salt with alkali metal such as sodium or potassium, with alkali earth metal such as calcium or magnesium or with metal such as aluminum or a salt with a base such as ammonia or organic amine. The salt as such may be produced from a free compound by a well known method or may be converted each other.

The present compound includes optical isomers thereof and, when it exists in a form of hydrate, solvate or complex compound, the present invention covers any of them. With regard to crystal polymorphism of the present compound, it has been known that crystals of type I and type II exist and the present compound includes various crystal forms (crystal polymorphism) being able to be formed including the above crystal forms. Production process and crystal polymorphism of the present compound are disclosed in Japanese Patent Laid-Open No. Sho-57-114,578, International Publication WO 03/084,934, etc.

The present compound may be made into a pharmaceutical preparation wherein various pharmaceutical additives suitable for the dosage form such as excipient, binder, wetting agent, disintegrating agent, lubricant and diluent are combined as necessary. Among them, the dosage form which is most simple and convenient for a patient is an oral preparation. As to the oral preparation, it is possible to make into a dosage form such as tablets, capsules, diluted powder, granules, liquid and syrup.

With regard to the additive for making into an oral preparation, there may be exemplified excipient, binder, disintegrating agent and lubricant. Examples of the excipient include saccharide such as lactose, sugar alcohol such as mannitol, crystalline cellulose, corn starch and potato starch. Examples of the binder include hydroxypropylmethylcellulose, hydroxypropylcellulose, alpha-starch, polyvinylpyrrolidone, pullulan, crystalline cellulose, cellulose derivatives, gum arabic, corn starch and gelatin. Examples of the disintegrating agent include carmellose, carmellose calcium, carboxymethyl starch sodium, low substituted hydroxypropylcellulose, crospovidone, croscarmellose sodium, corn starch, potato starch and carboxymethylcellulose potassium. Examples of the lubricant include talc, magnesium stearate, sucrose esters of fatty acids, hydrogenated oil and stearic acid. In addition to the above, extender, wetting agent, buffer, preservative, flavoring, etc. may be appropriately combined therewith and corrigent, aromatizing agent, etc. may also be added thereto. In the case of tablets, it is also possible to make into a film-coated tablet, etc. where a coat is applied to a plain tablet using an appropriate coating agent such as a polymer compound. As to the coating agent, there may be used a commonly used one such as hydroxypropylmethylcellulose, hydroxypropylcellulose, methylcellulose or polyvinylpyrrolidone. As to a coating aid, there may be used polyethylene glycol 6000, polysorbate, titanium oxide or dye such as red iron oxide, etc.

An example of the formulations for the manufacture of the present pharmaceutical agent in a form of tablets where each tablet contains 400 mg of the present compound is shown below, although the present invention shall not be limited thereto at all.

|  | (mg/tablet) |
|---|---|
| [Plain tablet] | |
| Present compound | 400.0 |
| Calcium citrate | 80.0 |
| Crystalline cellulose | 94.0 |
| Hydroxypropylcellulose | 8.0 |
| Carmellose calcium | 6.0 |
| Talc | 6.0 |
| Magnesium stearate | 6.0 |
| (Subtotal) | 600.0 |
| [Coat] | |
| Hydroxypropylcellulose | 11.0 |
| Macrogol 6000 | 2.2 |
| Crystalline cellulose | 3.2 |
| Titanium oxide | 1.6 |
| (Subtotal) | 18.0 |
| (Grand total) | 618.0 |

The preferred dose of the present compound may vary depending upon the object to be administered (age, body weight, etc. of a patient), type and degree of the disease, dosage form, administering method, administering period, etc. However, according to the result of the clinical test mentioned in the following Examples, 800±200 mg, preferably 800±100 mg or, more preferably, 800 mg of the present compound may be usually administered to an adult as a dose for one day in order to achieve the desired effect by oral administration to humans. The above daily dose may be administered either at a time or by dividing into two or three times.

EXAMPLES

Now the result of the clinical test using the present agent (where the dosage form is a tablet) will be shown as hereunder. Firstly, the result of the clinical test conducted in the past is shown as a Referential Example. Then, the result of the clinical test conducted recently is shown as an Example whereby the significance of the present invention is specifically illustrated, although the present invention shall not be limited at all by them.

Referential Example—Result of the Clinical Tests (1)

The clinical tests shown in Non-Patent Documents 1 and 2 will be explained as follows. Non-Patent Document 2 is a follow-up report of the clinical test of Non-Patent Document 1. As hereinafter, the clinical tests concerning those documents will be referred to as the "old clinical tests".

In the old clinical tests, a test drug was orally administered once daily for 24 weeks where an object was a patient with diabetic CRF and then the efficacy and the safety of the present compound were evaluated. Persons who were the patients receiving a conservative therapy for diabetic CRF and meet the following selection criteria were selected as test subjects.

1) The sCr value is 1.5 mg/dL or more and continues to increase consistantly.
2) Creatinine clearance is less than 50 mL/minute.
3) A person is suffer from diabetic neuropathy.

Results of the old clinical tests were compared by means of the changes in the reciprocal inclination of sCr values in a test subject before and after the administration of the test drug.

There is the following disclosure in Non-Patent Document 2 for the outline and the result of the old clinical tests. ("Pharmaceutical agent" in Patent Document 2 means a tablet containing the present compound. Incidentally, there are some passages therein where this pharmaceutical agent or the present compound is expressed in a development number reading "NZ-419".)

"Twenty-six cases were registered (55.8 years old in average) and divided into two groups comprising a 200 mg administered group (13 cases) and a 400 mg administered group (13 cases). In four cases, complicating symptoms became worse and were dropped. Clinical effect was evaluated by means of the reciprocal sCr value (1/sCr). During the period of more than three months before the administration of the pharmaceutical agent, the sCr values were measured for at least five times and adopted as a control value of a test subject. The sCr value immediately before the first administration of the pharmaceutical agent was within a range of 1.7 to 4.0 mg/dL. After administering the pharmaceutical agent, the sCr values were measured in the second, fourth, eighth, twelfth, sixteenth, twentieth and twenty-fourth weeks. The 1/sCr values versus time were plotted and a regression line was prepared by means of the least-square method. Changes in the inclination of the regression line were compared at the stages of before and after administering the pharmaceutical agent. The following differences were noted statistically significantly and they show that steepness of the inclination was relieved by the pharmaceutical agent.

200 mg/day administered group (n=11): −0.00075±0.00066 before the administration and −0.00046±0.00043 after the administration (p=0.01)

400 mg/day administered group (n=11): −0.00098±0.00077 before the administration and −0.00066±0.00097 after the administration (p=0.02)

(Mean value±S. D.)

No critical side effect by the pharmaceutical agent was noted in the clinical test and in the clinical symptom. During the course of the clinical test, no accumulation of the pharmaceutical agent was noted."

The above result made into a graph is FIG. 1.

In Non-Patent Document 1, the part of the final result is as mentioned below and that is the difference from Non-Patent Document 2.

"200 mg/day administered group (n=12: −0.00078±0.00064 before the administration and −0.00040±0.00047 after the administration (p=0.016)

400 mg/day administered group (n=11): −0.00098±0.00077 before the administration and −0.00068±0.00096 after the administration (p=0.024)"

Example—Result of the Clinical Test (2)

Results of the old clinical tests show a certain effect of the present compound to the diabetic CRF. However, as will be understood from FIG. 1, it was evaluated that the effect was not so surprisingly significant. Therefore, development of the present compound as a therapeutic agent for diabetic CRF or CKD had been ceased.

During such a period, a good idea has occurred that the effect of the present compound is investigated after dividing the patients with CKD into groups where worsening of the renal function is rapid and is not. As a result, the patients with CKD were divided into a group where changes in the reciprocal sCr value (1/sCr) per month before administration of the test drug are 0.01 dL/mg or more and worsening of the renal function is rapidly progressing (hereinafter, that will be referred to as "rapidly progressive CKD patients") and another group where said changes are less than 0.01 dL/mg (hereinafter, that will be referred to as "slowly progressive CKD patients") and clinical tests comparing the effect of the present compound were carried out. (Hereinafter, that will be referred to as "new clinical tests".) Such a yardstick where the changes in the reciprocal sCr value are 0.01 dL/mg or more followed the yardstick adopted in the application of "Kremezin (Registered Trade Mark)" which is the above-mentioned spherical adsorptive carbon preparation. Further, in the new clinical tests, dose of the present compound was increased to some extent so as to find the difference from the results in the old clinical tests. Summary and result of the new clinical tests will be mentioned as follows.

A clinical test for evaluating the efficacy and the safety of the present compound was conducted using the patients where the CKD stage was 3 or 4 as the object. Persons who meet the following selection criteria were selected from the patients who were diagnosed as CKD and receiving a conservation therapy.

Sex is withdrawn from the consideration. Pregnant women and mothers suckling a baby are however excluded.

Age is from 20 to 75 years old.

GFR value is 15 to 59.

Patients where the serum creatinine (sCr) value is within a range of 1.5 to 5.0 mg/dL at the start of the test, the measuring frequencies from 52 weeks before the test until the start of the test are thrice or more and the difference in the tested values in the initial and the final stages is 0.2 mg/dL or more (showing a rise).

Patients where a therapy with a pharmaceutical agent which is thought to suppress the progress of CKD (such as a spherical adsorptive carbon preparation) or a diet therapy is newly started during three month before the start of the test are excluded.

Moreover, patients having a symptom of cerebrovascular disturbance, patients with infectious disease and patients with peptic ulcer are excluded.

After that, the objects were divided into the rapidly-progressive CKD patients and slowly-progressive CKD patients.

As a result, in the new clinical tests, the groups to which the tablets containing the present compound as an active ingredient (test drug) are administered and to which the tablets containing no active ingredient though being undistinguishable from the test drug are divided into six groups in total. Thus, they are three groups for slowly-progressive CKD patients comprising a placebo-administered group, a 800 mg test drug-administered group and a 1600 mg test drug-administered group and other three groups for a rapidly-progressive CKD patients comprising a placebo-administered, a 800 mg test drug-administered group and a 1600 mg test drug-administered group whereby there are six groups in total. The weight mentioned hereinabove is a weight of the present compound contained in the test drug and is a dose for one day. Incidentally, in the new clinical tests, administration was done once daily. A test drug containing 400 mg of the present compound per tablet was used. Therefore, administration of a 800-mg test drug means that two tablets of the test drug are administered and administration of a 1600-mg test drug means that four tablets of the test drug are administered. In a placebo, lactose is used as a substitute for the present compound which is an active ingredient and adjustment with the amount of another additive was done so that the total weight is made the same as that of the test drug. Both of the test drug and the placebo are called "investigational drug".

The investigational drug was orally administered to test subjects once daily during 24 weeks. The administering time was made 30 minutes before breakfast if at all possible. Inclinations of the regression line to the reciprocal sCr values (1/sCr) before and after administration of the investigational drug were compared to evaluate the effect of the investigational drug for the progress of CKD. Test of significance was done by means of Dunnett test.

To be more specific, changes in the renal function between the stage of 24 weeks before the administration of the investigational drug and the stage of 24 weeks after the start of the administration were evaluated by means of the inclination of a regressive line to the reciprocal sCr values (1/sCr). As a result, progress of worsening of the renal function in a rapidly-progressive CKD patient was significantly suppressed or improved by administration of 800 mg/day of the present compound as shown in FIG. 2. This result was found to be statistically significant as well. No such an effect was achieved in a slowly-progressive CKD patient showing the selectiveness to a rapidly-progressive CKD patient. In a 1600 mg/day-administered group, a certain effect was noted in a rapidly-progressive CKD patient but the effect was not so significant. No effect was noted in a slowly-progressive CKD patient. In a group where a placebo was administered to a quickly-progressive CKD patient, no change in the renal function was noted at all.

The outcome where the above result is shown in terms of changes in the reciprocal inclination of sCr values is FIG. 3. In the rapidly-progressive CKD patient group, the downward-sloping inclination does not change at all between before and after the treatment in a placebo-administered group (average of five test subjects) while, in the 800 mg present compound-administered group (average of five test subjects), a downward-sloping inclination becomes somewhat upward rather than moderate whereby the progress of the renal function decrease is suppressed or improved (solid line in the graph of the right hand side in FIG. 3). Although the case numbers are limited, this result exceeds the effect of the above "Kremezin (Registered Trade Mark)". For reference, changes in all of the reciprocal inclinations of sCr values for five test subjects in a placebo-administered group and for five test subjects in a 800 mg/day test drug-administered group among the rapidly-progressive CKD patients are shown in FIG. 4. It is noted from FIG. 4 that worsening of the renal function in all of the five test subjects in a 800 mg/day test drug-administered group is significantly suppressed or improved. On the other hand, it is noted that worsening of the renal function in the five test subjects in a placebo-administered group is not suppressed at all (no change is noted) (solid line in the graph of the left hand side in FIG. 3). Incidentally, in all of the cases including the 1600 mg/day-administered group, no critical side effect becoming a problem is observed whereby it has been recognized that the present pharmaceutical agent is of very high safety.

As mentioned already, for rapidly-progressive CKD patients, there is no therapeutic agent which is effective for suppressing the progress of the renal function decrease and is simply and conveniently ingestible. Under such circumstances, the effect of the present compound is prominent and the renal function can be kept almost in a state of upon the start of the therapy whereby the period for introducing the dialysis can be greatly extended and, in some cases, avoidance thereof can be expected. As a result, it is a matter of course that prevention of lowering of QOL of a patient is achieved and there is also a possibility of extending the survival period. Generally, drug therapy achieves its effect when administration is done before the symptom becomes critical and there are many cases where the outcome is not so effective when the symptom becomes critical. However, as shown in FIGS. 2 to 4, the present compound has such a specific effect that it is not achieved in a slowly-progressive CKD patient where the symptom is not yet critical but is achieved in a rapidly-progressive CKD patient where the early introduction of dialysis is felt uneasy. Incidentally, if the period for introducing the dialysis of the rapidly-progressive CKD patient can be retarded, there is also a possibility that it is effective for suppressing the increase in the national medical expenses.

INDUSTRIAL APPLICABILITY

5-Hydroxy-1-methylhydantoin which is the active ingredient of the present pharmaceutical agent showed a significant effect to a patient where worsening of the renal function rapidly proceeds among the patients with CKD. The present pharmaceutical agent can suppress or improve the worsening of the renal function in the above patient where no effective therapeutic agent being able to be easily administered has been available and the agent also shows high safety and is easily ingestible whereby it has a quite high usefulness.

The invention claimed is:

1. A method of suppressing or improving chronic kidney disease comprising administering to a patient with chronic kidney disease in which a rise in the reciprocal serum creatinine value per month is 0.01 dL/mg or more a pharmaceutical agent containing 5-hydroxy-1-methylimidazolidin-2,4-dione as an active ingredient, wherein the pharmaceutical agent is orally administered to the patient in a dose of 800±200 mg of 5-hydroxy-1-methylimidazolidin-2,4-dione per day.

2. The method according to claim 1, wherein the dose is 800±100 mg per day.

3. The method according to claim 1, wherein the dose is 800 mg per day.

4. The method according to claim 1, wherein the patient with chronic kidney disease is in a stage 3 or 4 of the chronic kidney disease.

5. The method according to claim 4, wherein the pharmaceutical agent is orally administered once daily.

6. The method according to claim 1, wherein the pharmaceutical agent is in a form of a tablet.

7. The method according to claim 1, wherein the 5-hydroxy-1-methylimidazolidin-2,4-dione is in a form of a salt, an optical isomer, a crystal polymorph, a hydrate, a solvate or a complex.

8. A pharmaceutical product comprising 5-hydroxy-1-methylimidazolidin-2,4-dione as an active ingredient, wherein the product administers a total of 800±200 mg of the 5-hydroxy-1-methylimidazolidin-2,4-dione per day.

9. The pharmaceutical product according to claim 8, wherein the product administers 800±100 mg of the 5-hydroxy-1-methylimidazolidin-2,4-dione per day.

10. The pharmaceutical product according to claim 8, wherein the product administers 800 mg of the 5-hydroxy-1-methylimidazolidin-2,4-dione per day.

* * * * *